United States Patent
Lu et al.

(10) Patent No.: US 6,380,421 B1
(45) Date of Patent: Apr. 30, 2002

(54) MULTIDENTATE PHOSPHITE LIGANDS, CATALYTIC COMPOSITIONS CONTAINING SUCH LIGANDS AND CATALYTIC PROCESSES UTILIZING SUCH CATALYTIC COMPOSITIONS

(75) Inventors: Helen S. M. Lu, Wallingford; Nora Radu, Landenberg, both of PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/651,878

(22) Filed: Aug. 30, 2000

Related U.S. Application Data

(60) Provisional application No. 60/154,882, filed on Sep. 20, 1999.

(51) Int. Cl.[7] .......................................... C07C 253/10
(52) U.S. Cl. .................................. 558/334; 558/338
(58) Field of Search ............................... 558/334, 338

(56) References Cited

U.S. PATENT DOCUMENTS

| | | |
|---|---|---|
| 3,496,210 A | 2/1970 | Drinkard, Jr. et al. |
| 3,496,217 A | 2/1970 | Drinkard, Jr. et al. |
| 3,496,218 A | 2/1970 | Drinkard, Jr. et al. |
| 3,631,191 A | 12/1971 | Kane et al. |
| 3,655,723 A | 4/1972 | Drinkard, Jr. |
| 3,846,461 A | 11/1974 | Shook, Jr. |
| 3,847,959 A | 11/1974 | Shook, Jr. et al. |
| 3,903,120 A | 9/1975 | Shook, Jr. et al. |
| 3,907,847 A | 9/1975 | Keblys |
| 4,774,353 A | 9/1988 | Halb et al. |
| 4,874,884 A | 10/1989 | McKinney et al. |
| 5,210,260 A | 5/1993 | Böhshar et al. |
| 5,235,113 A | 8/1993 | Sato et al. ................. 568/454 |
| 5,512,696 A | 4/1996 | Kreutzer et al. ........... 558/338 |
| 5,663,369 A | 9/1997 | Kreutzer et al. ........... 549/212 |
| 5,668,986 A | 9/1997 | Tam et al. ................. 558/338 |
| 5,710,344 A | 1/1998 | Breikss et al. ............. 568/454 |
| 5,723,641 A | 3/1998 | Tam et al. .................. 556/13 |
| 5,821,378 A | 10/1998 | Foo et al. ................... 558/338 |
| 5,847,191 A | 12/1998 | Bunel et al. ................ 558/338 |
| 5,874,641 A | 2/1999 | Burke et al. ................ 568/454 |
| 5,910,600 A | 6/1999 | Urata et al. ................ 558/162 |

FOREIGN PATENT DOCUMENTS

| | | | |
|---|---|---|---|
| JP | 62077341 | 4/1987 | |
| WO | WO 95/30680 | 11/1995 | |
| WO | WO 96/11182 | 4/1996 | |
| WO | WO 96/22968 | 8/1996 | |
| WO | WO 97/33854 | 9/1997 | ........... C07C/45/50 |
| WO | WO 99/06355 | 2/1999 | |
| WO | WO 99/06357 | 2/1999 | ......... C07C/253/10 |
| WO | WO 99/06358 | 2/1999 | |

OTHER PUBLICATIONS

T. Jongsma, et al., "A New Type of Highly Active Polymer–Bound Rhodium Hydroformylation Catalyst", Polymer, vol. 33, No. 1, pp. 161–165, 1992.

William H. Pirkle, et al., "Chiral High–Pressure Liquid Chromatographic Stationary Phases. 4. Separation of the Enantiomers of Bi–B–naphthols and Analogues", J. Org. Chem, 46 pp. 4988–4991, 1981.

Gregory D. Cuny, et al., Practical High–Yield, Regioselective, Rhodium–Catalyzed Hydroformylation of Functionalized a–Olefins, J. Am. Chem. Soc. 115, pp. 2066–2068, 1983.

Klaus B. Simonsen et al., "A Simple Synthetic Approach to 3,3'–Diaryl BINOLs", J. Org. Chem., vol. 63, No. 21, pp. 7536–7538, 1998.

Gloede, et al. "Zur Halogenierung der o–Methoxyphenylester von P"–Säuren, Z. anorg.allg.Chem., 538, pp. 221–228 (1986).

Warren W. Kaeding, "Oxidation of Phenols with Cupric Salts", J. Org. Chem., vol. 28, pp. 1063–1067 (1963).

*Primary Examiner*—Floyd D. Higel
*Assistant Examiner*—Ebenezer Sackey

(57) ABSTRACT

Hydrocyanation reactions employing multidentate phosphite ligands and multidentate phosphite ligands are disclosed. The ligands have phenyl containing substituents attached to the ortho position of the terminal phenol group and/or attached to the ortho position of the bridging group. Catalyst compositions havng such ligands achieve 97% or greater distribution in hydrocyanation.

18 Claims, No Drawings

MULTIDENTATE PHOSPHITE LIGANDS, CATALYTIC COMPOSITIONS CONTAINING SUCH LIGANDS AND CATALYTIC PROCESSES UTILIZING SUCH CATALYTIC COMPOSITIONS

This application claims the benefit to U.S. Provisional Application No. 60/154,882 filed Sep. 20, 1999.

FIELD OF THE INVENTION

The invention relates to certain multidentate phosphite ligands, the catalyst compositions made therefrom and a catalytic hydrocyanation process which employs such multidentate phosphite ligands. In particular, the ligands have phenyl containing substituents attached to the ortho position of the terminal phenol group and/or attached to the ortho position of the backbone.

TECHNICAL BACKGROUND OF THE INVENTION

Phosphorus ligands are ubiquitous in catalysis and are used for a number of commercially important chemical transformations. Phosphorus ligands commonly encountered in catalysis include phosphines (A), and phosphites (B), shown below. In these representations, R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

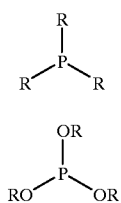

There are several industrially important catalytic processes employing phosphorus ligands. For example, U.S. Pat. No. 5,910,600 to Urata, et al. discloses that bisphosphite compounds can be used as a constituting element of a homogeneous metal catalyst for various reactions such as hydrogenation, hydroformylation, hydrocyanation, hydrocarboxylation, hydroamidation, hydroesterification and aldol condensation.

Some of these catalytic processes are used in the commercial production of polymers, solvents, plasticizers and other commodity chemicals. Consequently, due to the extremely large worldwide chemical commodity market, even small incremental advances in yield or selectivity in any of these commercially important reactions are highly desirable. Furthermore, the discovery of certain ligands that may be useful for applications across a range of these commercially important reactions is also highly desirable not only for the commercial benefit, but also to enable consolidation and focusing of research and development efforts to a particular group of compounds.

U.S. Pat. No. 5,512,696 to Kreutzer, et al. discloses a hydrocyanation process using a multidentate phosphite ligand, and the patents and publications referenced therein describe hydrocyanation catalyst systems pertaining to the hydrocyanation of ethylenically unsaturated compounds. U.S. Pat. Nos. 5,723,641, 5,663,369, 5,688,986 and 5,847,191 disclose processes and catalyst compositions for the hydrocyanation of monoethylenically unsaturated compounds using zero-valent nickel and multidentate phosphite ligands, and Lewis acid promoters.

U.S. Pat. No. 5,821,378 to Foo, et al. discloses a liquid phase process for the hydrocyanation of diolefinic compounds to produce nonconjugated acyclic nitriles as well as a liquid phase process for the isomerization of those nitriles to 3- and/or 4-monoalkene linear nitriles where the reactions are carried out in the presence of zero-valent nickel and a multidentate phosphite ligand. Other catalytic processes for the hydrocyanation of olefins and the isomerization of monoalkene nitriles are described in the patents and publications referenced therein. Commonly assigned, published PCT Application WO99/06357 discloses multidentate phosphite ligands having alkyl ether substituents on the carbon attached to the ortho position of the terminal phenol group for use in a liquid phase process for the hydrocyanation of diolefinic compounds to produce nonconjugated acyclic nitrites as well as a liquid phase process for the isomerization of those nitrites to 3- and/or 4-monoalkene linear nitrites.

The use of multidentate phosphate ligands having binaphthalene and/or biphenyl bridging groups for hydroformylation reactions is disclosed in U.S. Pat. Nos. 5,235,113, 5,874,641, 5,710,344 and published PCT Application WO 97/33854

While the catalyst systems described above may represent commercially viable catalysts, it always remains desirable to provide even more effective, higher performing catalyst precursor compositions, catalytic compositions and catalytic processes to achieve full commercial potential for a desired reaction. The effectiveness and/or performance may be achieved in any or all of rapidity, selectivity, efficiency or stability, depending on the reaction performed. It is also desirable to provide such improved catalyst systems and/or processes which may be optimized for a commercially important reaction such hydrocyanation or isomerazation. Other objects and advantages of the present invention will become apparent to those skilled in the art upon reference to the detailed description which hereinafter follows.

SUMMARY OF THE INVENTION

The invention provides for a hydrocyanation process comprising reacting an acyclic, aliphatic, monoethylenicaly unsaturated compound in which the ethylenic double bond is not conjugated to any other olefinic group in the molecule with a source of HCN in the presence of a catalyst composition comprising a Lewis acid, a zero-valent nickel and at least one multidentate phosphite ligand selected from the group represented by the following formulae I II or III, in which all like reference characters have the same meaning, except as further explicitly limited.

Formula I

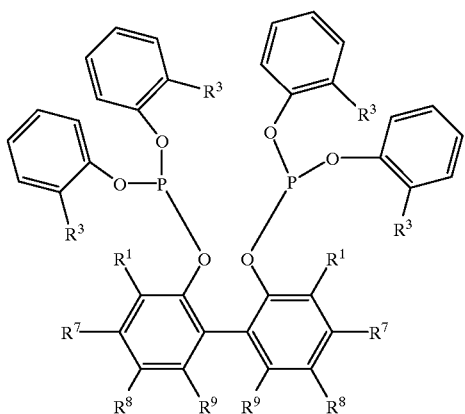

Formula II

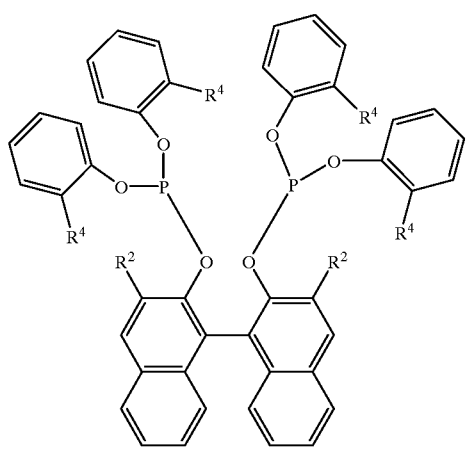

Formula III

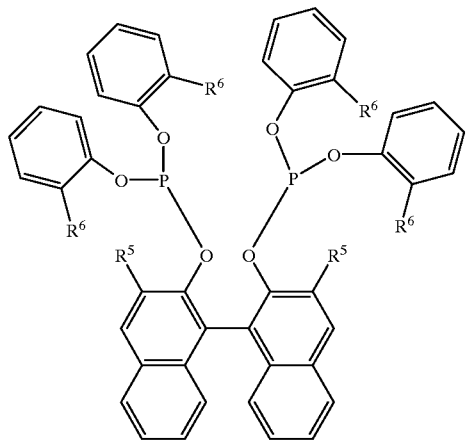

wherein
R$^1$ is independently C$_1$ to C$_{18}$ primary or secondary alkyl;
R$^2$ is independently aryl or substituted aryl;
R$^3$ is independently aryl or substituted aryl;
R$^4$ is independently C$_1$ to C$_{18}$ primary alkyl;
R$^5$ is hydrogen;
R$^6$ is independently aryl or substituted aryl;
R$^7$ is independently C$_1$ to C$_{18}$ primary or secondary alkyl;
R$^8$ is independently C$_1$ to C$_{18}$ primary or secondary alkyl; and
R$^9$ is independently C$_1$ to C$_{18}$ primary or secondary alkyl;

wherein other positions on the aromatic rings may also be substituted with alkyl, ether or ester groups, or combinations of two or more thereof.

The invention also provides for a multidentate phosphite ligand having the structure represented by the following Formula I, II or III in which all like reference characters have the same meaning, except as further explicitly limited.

Formula I

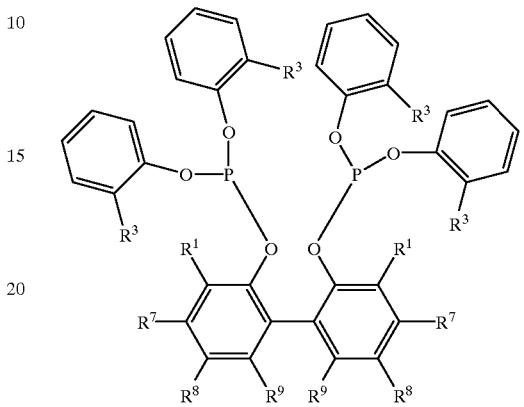

Formula II

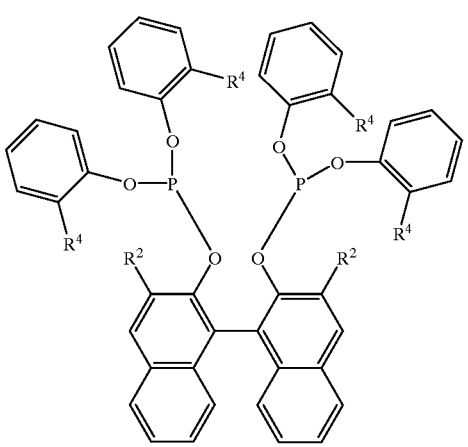

Formula III

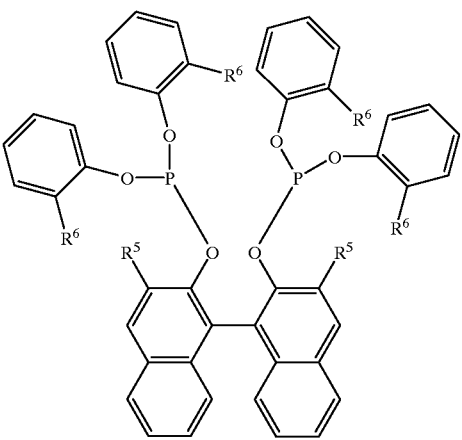

wherein
R$^1$ is independently C$_1$ to C$_{18}$ primary or secondary alkyl;
R$^2$ is independently aryl or substituted aryl;
R$^3$ is independently aryl or substituted aryl;
R$^4$ is independently C$_1$ to C$_{18}$ primary alkyl;
R$^5$ is hydrogen;

$R^6$ is independently aryl or substituted aryl;

$R^7$ is independently $C_1$ to $C_{18}$ primary or secondary alkyl;

$R^8$ is independently $C_1$ to $C_{18}$ primary or secondary alkyl; and $R^9$ is independently $C_1$ to $C_{18}$ primary or secondary alkyl;

wherein other positions on the aromatic rings may also be substituted with alkyl, ether or ester groups, or combinations of two or more thereof.

DETAILED DESCRIPTION OF THE PREFERRED EMBODIMENTS

The invention provides for certain multidentate phosphite ligands, improved catalyst systems employing such ligands, and the use of such multidentate phosphite ligands in hydrocyanation reactions.

The catalyst compositions useful in the invention preferably are comprised of a multidentate phosphite ligand of formula I, II and III and a transition metal.

Formula I

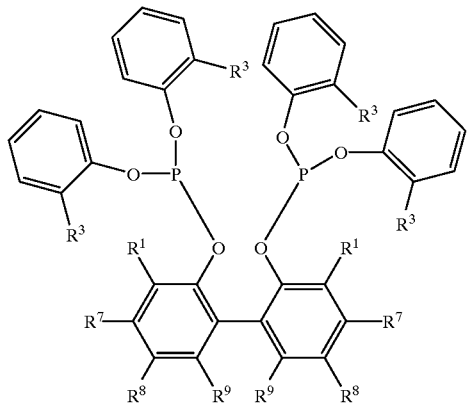

Formula II

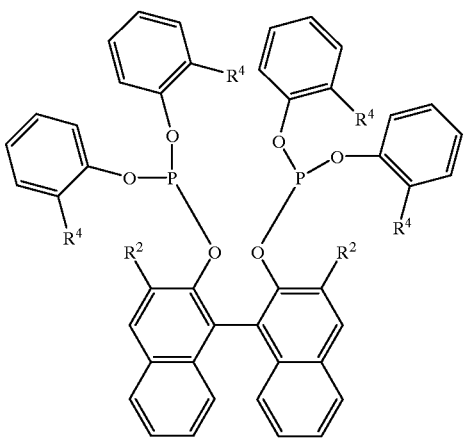

Formula III

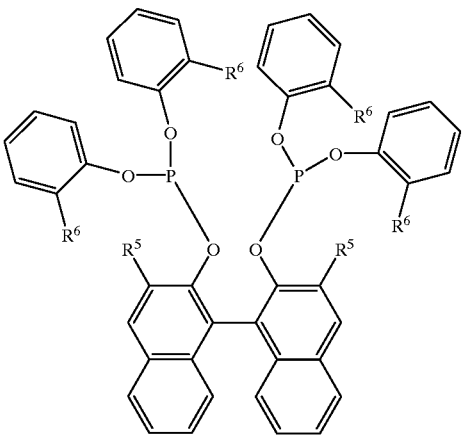

wherein $R^1$ is independently $C_1$ to $C_{18}$ primary alkyl;

$R^2$ is independently aryl or substituted aryl;

$R^3$ is independently aryl or substituted aryl;

$R^4$ is independently $C_1$ to $C_{18}$ primary alkyl;

$R^5$ is hydrogen;

$R^6$ is independently aryl or substituted aryl;

$R^7$ is independently $C_1$ to $C_{18}$ primary or secondary alkyl;

$R^8$ is independently $C_1$ to $C_{18}$ primary or secondary alkyl; and $R^9$ is independently $C_1$ to $C_{18}$ primary or secondary alkyl;

wherein other positions on the aromatic rings may also be substituted with alkyl, ether or ester groups, or combinations of two or more thereof.

The divalent bridging compounds used in the ligands described in formulae I, II, and III may be prepared by a variety of methods known in the art. For example, 3,3',5,5'-tetramethyl-2,2'-biphenol can be prepared according to *J. Org. Chem.*, 1963, 28, 1063 and 3,3',5,5',6,6'-Hexamethyl-2,2'-biphenol can be prepared according to JP 85-216749. The 3,3'-diaryl-substituted 1,1'-2-naphthols can be obtained according to *J. Org. Chem.*, 1998, 63, 7536.

Phosphorochloridite may be prepared by a variety of methods known in the art, for example, see descriptions in *Polymer*, 1992, 33, 161; *Inorganic Synthesis*, 1966, 8, 68; U.S. Pat. No. 5,210,260; *Z. Anorg. Allg. Chem.*, 1986, 535, 221. With ortho-substituted phenols, phosphorochloridites can be prepared in situ from $PCl_3$ and the phenol. Also, phosphorochloridites of 1-naphthols can be prepared in situ from $PCl_3$ and 1-naphthols in the presence of a base like triethylamine. Another process for preparing the phosphochlorodite comprises treatment of N,N-dialkyl diarylphosphoramidite with HCl. $ClP(OMe)_2$ has been prepared in this manner, see *Z. Naturforsch*, 1972, 27B, 1429. Phosphorochloridites derived from substituted phenols have been prepared using this procedure as described in commonly assigned U.S. Pat. No. 5,821,378.

By contacting the thus obtained $(OAr)_2PCl$, wherein Ar is a substituted aryl, with a divalent bridging compound, for example by the method described in U.S. Pat. No. 5,235,113, a bidentate phosphite ligand is obtained which can be used in the process according to the invention.

The transition metal may be any transition metal capable of carrying out catalytic transformations and may additionally contain labile ligands which are either displaced during the catalytic reaction, or take an active part in the catalytic transformation. Any of the transition metals may be considered in this regard. The preferred metals are those comprising group VIII of the Periodic Table. The preferred metals for hydroformylation are rhodium, cobalt, iridium, ruthenium, palladium and platinum. The preferred metals for hydrocyanation and/or isomerization are nickel, cobalt, and palladium, and nickel is especially preferred for hydrocyanation.

The catalyst compositions of the invention are comprised of at least one multidentate phosphite ligand according to any one of formulae I, II and III and a transition metal. In embodiments of the invention, catalyst compositions useful for processes such as hydroformylation may have Group VIII compounds such as can be prepared or generated according to techniques well known in the art, as described, for example, WO 95 30680, U.S. Pat. No. 3,907,847, and *J. Amer. Chem. Soc.*, 1993, 115, 2066. Examples of such suitable Group VIII metals are ruthenium, rhodium, and iridium. Suitable Group VIII metal compounds are hydrides, halides, organic acid salts, acetylacetonates, inorganic acid salts, oxides, carbonyl compounds and amine compounds of these metals. Examples of suitable Group VIII metal compounds are, for example, $Ru_3(CO)_{12}$, $Ru(NO_3)_2$, $RuCl_3$ $(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The Group VIII metal is preferably rhodium. Rhodium compounds that contain ligands which can be displaced by the multidentate phosphites are a preferred source of rhodium. Examples of such preferred rhodium compounds are $Rh(CO)_2$ (acetylacetonate), $Rh(CO)_2(C_4H_9COCHCO-t-C_4H_9)$, $Rh_2O_3$, $Rh_4(CO)_{12}$, $Rh_6(CO)_{16}$, $Rh(O_2CCH_3)_2$, and $Rh(2\text{-ethylhexanoate})$. Rhodium supported on carbon may also be used in this respect.

Nickel compounds can be prepared or generated according to techniques well known in the art, as described, for example, in U.S. Pat. Nos. 3,496,217; 3,631,191; 3,846,461; 3,847,959; and 3,903,120, which are incorporated herein by reference. Zero-valent nickel compounds that contain ligands which can be displaced by the organophosphorus ligand are a preferred source of nickel. Two such preferred zero-valent nickel compounds are $Ni(COD)_2$ (COD is 1,5-cyclooctadiene) and $Ni\{P(O\text{-}o\text{-}C_6H_4CH_3)_3\}_2(C_2H_4)$, both of which are known in the art. Alternatively, divalent nickel compounds may be combined with a reducing agent, to serve as a source of nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

Depending upon the desired reaction to be performed, the catalyst composition of this invention may also include the presence of one or more Lewis acid promoters, which affect both the activity and the selectivity of the catalyst system. The promoter may be an inorganic or organometallic compound in which the at least one of the elements of said inorganic or organometallic compound is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(TBF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(\text{iso-}C_4H_9)_2AlCl$, $Ph_2AlCl$, $PhAlC_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

HYDROCYANATION OF MONOOLEFINIC COMPOUNDS

The present invention provides for a process of hydrocyanation, comprising reacting an unsaturated compound with a source of hydrogen cyanide in the presence of a catalyst composition comprising a transition metal selected from Ni, Co, and Pd, and a Lewis acid compound, and at least one ligand selected from the group represented by formulae I, II, or III. Representative ethylenically unsaturated compounds which are useful in the hydrocyanation process of this invention are shown in Formulae IV or V, and the corresponding terminal nitrile compounds produced are illustrated by Formulae IV or VI, respectively, wherein like reference characters have same meaning.

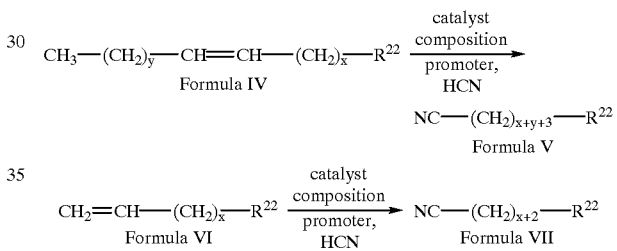

wherein
$R^{22}$ is H, CN, $CO_2R^{23}$, or perfluoroalkyl;
y is an integer of 0 to 12;
x is an integer of 0 to 12 when $R^{22}$ is H, $CO_2R^{23}$ or perfluoroalkyl;
x is an integer of 1 to 12 when $R^{22}$ is CN; and
$R^{23}$ is $C_1$ to $C_{12}$ alkyl, or aryl.

The nonconjugated acyclic, aliphatic, monoethylenically unsaturated starting materials useful in this invention include unsaturated organic compounds containing from 2 to approximnately 30 carbon atoms. Suitable unsaturated compounds include unsubstituted hydrocarbons as well as hydrocarbons substituted with groups which do not attack the catalyst, such as cyano. Examples of these monoethylenically unsaturated compounds include ethylene, propylene, 1-butene, 2-pentene, 2-hexene, etc., nonconjugated diethylenically unsaturated compounds such as allene, substituted compounds such as 3-pentenenitrile, 4-pentenenitrile, methyl pent-3-enoate, and ethylenically unsaturated compounds having perfluoroalyl substituents such as, for example, $C_zF_{2z+1}$, where z is an integer of up to 20. The monoethylenically unsaturated compounds may also be conjugated to an ester group such as methyl pent-2-enoate. Preferred are nonconjugated linear alkenes, nonconjugated linear Allen-nitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}$ $CH=CH_2$ (where z is 1 to 12).

3-Pentenenitrile and 4-pentenenitrile are especially preferred. As a practical matter, when the nonconjugated acyclic aliphatic monoethylenically unsaturated compounds are used in accordance with this invention, up to about 10% by weight of the monoethylenically unsaturated compound may be present in the form of a conjugated isomer, which itself may undergo hydrocyanation. For example, when 3-pentenenitrile is used, as much as 10% by weight thereof may be 2-pentenenitrile. (As used herein, the term "pentenenitrile" is intended to be identical with "cyanobutene").

The preferred products are terminal alkanenitriles, linear dicyanoalkylenes, linear aliphatic cyanoesters, and 3-(perfluoroalkyl) propionitrile. Most preferred products are adiponitrile, alkyl 5-cyanovalerate, and $C_zF_{2z+1}CH_2CH_2CN$, where z is 1 to 12.

The present hydrocyanation process may be carried out, for example, by charging a reactor with the reactants, catalyst composition, and solvent, if any; but preferably, the hydrogen cyanide is added slowly to the mixture of the other components of the reaction. Hydrogen cyanide may be delivered as a liquid or as a vapor to the reaction. Another suitable technique is to charge the reactor with the catalyst and the solvent to be used, and feed both the unsaturated compound and the HCN slowly to the reaction mixture. The molar ratio of unsaturated compound to catalyst can be varied from about 10:1 to about 2000:1.

Preferably, the reaction medium is agitated, for example, by stirring or shaking. The reaction product can be recovered by conventional techniques such as, for example, by distillation. The reaction may be run either batchwise or in a continuous manner.

The hydrocyanation reaction can be carried out with or without a solvent. The solvent, if used, should be liquid at the reaction temperature and pressure and inert towards the unsaturated compound and the catalyst. Suitable solvents include hydrocarbons, such as benzene or xylene, and nitriles, such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from −25° C. to 200° C. can be used, the range of 0° C. to 150° C. being preferred.

Atmospheric pressure is satisfactory for carrying out the present invention and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the in which the at least one of the elements of said inorganic or organometallic compound is selected from scandium, titanium, vanadium, chromium, manganese, iron, cobalt, copper, zinc, boron, aluminum, yttrium, zirconium, niobiumn, molybdenum, cadmium, rhenium and tin. Examples include $ZnBr_2$, $ZnI_2$, $ZnCl_2$, $ZnSO_4$, $CuCl_2$, $CuCl$, $CU(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$ where $X=CF_3SO_3$, $CH_3C_6H_5SO_3$, or $(C_6H_5)_3BCN$. The mole ratio of promoter to nickel present in the reaction can be within the range of about 1:16 to about 50:1.

The invention will now be illustrated by the following non-limiting examples of certain embodiments thereof, wherein all parts, proportions, and percentages are by weight, unless otherwise indicated.

The following definitions are applicable wherever the defined terms appear in this specification:

The term "hydrocarbyl" designates a hydrocarbon molecule from which one hydrogen atom has been removed. Such molecules can contain single, double or triple bonds.
3PN: 3-pentenenitrile
2PN: 2-pentenenitrile
4PN: 4-pentenenitrile
2M3: 2-methyl-3-butenenitrile
VN: valeronitrile
ESN: ethylsuccinonitrile
MGN: 2-methylglutaronitrile
5FVN: 5-formylvaleronitrile
M3P: methyl 3-pentenoate
BD: 1,3-butadiene
COD: 1,5-cyclooctadiene
$Et_3N$: triethylamine
$PCl_3$: phosphorus trichloride
THF: tetrahydrofuran The protocol for calculating certain reaction results for hydrocyanation reactions and isomerization reactions follows:

For step 1 hydrocyanation reactions the % useful pentenenitriles (PN's) and the 3PN/2M3 ratio is reported. The product distribution is analyzed by gas chromatograph using valeronitrile as an internal standard. The % useful PN's is the molar ratio of the sum of 3PN(cis and trans) and 2M3 divided by the amount of HCN. The 3PN/2M3 ratio is the ratio of cis and trans 3PN to 2M3.

For step 2 hydrocyanation reactions the selectivity to adiponitrile (ADN) is ADN/(ESN+MGN+ADN). The 3PN and 4PN conversion is calculated using 2-ethoxyethylether (EEE) as an internal standard. The total conversion of pentenenitriles (PN's) to dinitriles (DN's), based on the assumption that all material is accounted for, is calculated as (sum (mol DN's)/sum (PN's+BN's+DN's)). (BN's are butenenitriles). The conversion based on HCN is calculated by dividing the total conversion of PN's to DN's by the HCN/PN ratio in the original feed, i.e., (mol DN/mol PN at sart)/(mol HCN/mol PN at start).

EXAMPLE 1

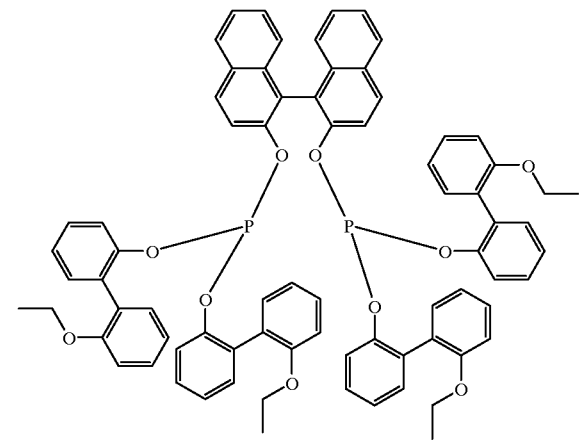

2'-Ethoxyl-1,1'-biphenyl-2-ol was prepared by modifying the procedure reported in *J. Org. Chem.* 1981, 46, 4988. In 50 mL of acetone was added 10 g of 2,2'-biphenol and 9.4 g of potassium carbonate. After stirring at room temperature for one hour, a solution of iodoethane (9.2 g in 10 mL of acetone) was added slowly dropwise. The mixture was filtered, washed with acetone, and solvent removed by rotary evaporation. The residue was flashed chromatographed to give 5.1 g of the2'-ethoxyl-1,1'-biphenyl-2-ol as a colorless oil. $^1$H NMR ($C_6D_6$): 7.20 (m, 3H), 7.10 (m, 1H), 7.05 (m, 1H), 6.85 (m, 2H), 6.55 (m, 1H), 3.38 (q, 2H), 0.81 (t, 3H).

In a nitrogen purged glove box, the above phenol (0.73 g, 3.40 mmol) was dissolved in 10 mL ether, and cooled to −30° C. To this was added cold (−30° C.) 1M phosphorous trichloride solution (1.7 mL), followed by dropwise addition of 1M triethylamine solution (4.0 mL). The solution was stirred at room temperature for 5 minutes, then kept at −30° C. for two hours. The reaction mixture was filtered through a pad of Celite® and concentrated to yield 0.67 g of the corresponding phosphorous chloridite. $^{31}$P NMR (toluene): 160.4 (78%), 126 (22%). The phosphorous chlorodite was reacted with 1,1'-bi-2-naphthol in the presence of triethylamine to yield ligand II. $^{31}$P NMR (toluene): 131.3 (major), 130.2.

EXAMPLE 2

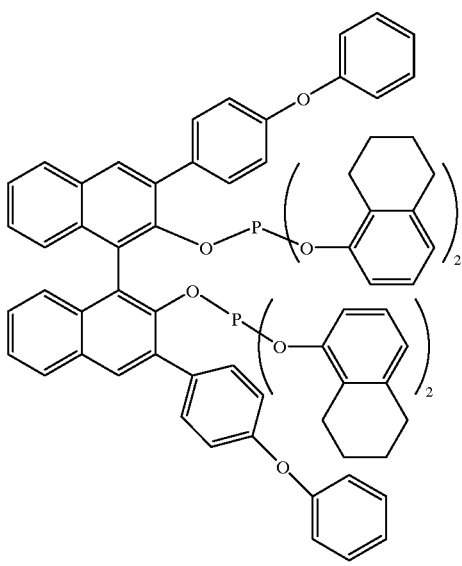

2,2'-dihydroxy-1,1'-binaphthalene-3,3'-bis (diphenylether) was prepared according to literature procedure reported in *J. Org. Chem.* 1998, 63, 7536). Under an atmosphere of nitrogen, a 250 mL two-necked Schlenk flask equipped with a reflux condenser was charged with 3,3'-bis (dihydroxyborane)-2,2'-dimethoxy-1,1'-binaphthyl (2.250 g, 5.60 mmol), Pd(PPh$_2$)$_4$ (0.360 g, 0.42 mmol), Ba(OH)$_2$ (5.25 g, 30.6 nunol), 4-bromo-diphenylether (4.47 g, 17.9 mmol), 1,4-dioxane (36 mL) and H$_2$O (12 mL). The reaction mixture was refluxed for 24 hours. Upon cooling to room temperature, the mixture was diluted with CH$_2$Cl$_2$ (150 mL) and washed with 1 N HCl (2×75 mL) and brine (2×75 mL). The solution was dried over MgSO$_4$. Removal of the solvent gave a brown oil, which was diluted in dry CH$_2$Cl$_2$ (125 mL) and cooled −40° C. Over a period of 10 min, BBr$_3$ (3 mL) was slowly added and the reaction mixture was stirred at room temperature overnight. The resulting red-brown solution was cooled to 0° C., and H$_2$O (300 mL) was carefully added. The organic layer was separated and then washed with H$_2$O (2×300 mL), 1 N HCl (300 mL) and brine (300 mL). The resulting solution was dried over MgSO$_4$ and concentrated. The resulting red oil was chromatographed on silica to give 2,2'-dihydroxy-1,1'-binaphthalene-3,3'-bis (diphenylether) as a white crystalline solid (0.80 g, 23%). [1]H (C$_6$D$_6$): 7.80 (s, 2H), 7.64 (d, J=8.2 Hz, 2H), 7.53 (d, J=8.7 Hz, 4H), 7.22 (d, J=8.3 Hz, 2H), 7.12 (m, 4H) 7.05–6.96 (m, 14H), 5.03 (s, 2H).

Under an atmosphere of nitrogen, a cold (−35° C.) anhydrous diethyl ether solution (20 mL) of 2,2'-dihydroxy-1,1'-binaphthalene-3,3'-bis(diphenylether) (0.405 g, 0.65 mmol) was added to the phosphochlorodite of 5,6,7,8-tetrahydro-1-naphthol (0.588 g, 1.63 mmol) dissolved in diethyl ether (10 mL). While maintaining this temperature, triethylamine (0.23 mL, 1.63 mmol) was added dropwise to the above mixture resulting in the formation of a white precipitate. After stirring at room temperature for three hours, the reaction mixture was filtered through a pad of basic alumina and Celite®. The filtrate was evaporated to yield the desired diphosphite as a white powder (0.537 g, 65%). $^{31}$P {$^1$H} NMR (202.4 MHz, C$_6$D$_6$): 132.75 ppm.

EXAMPLE 3

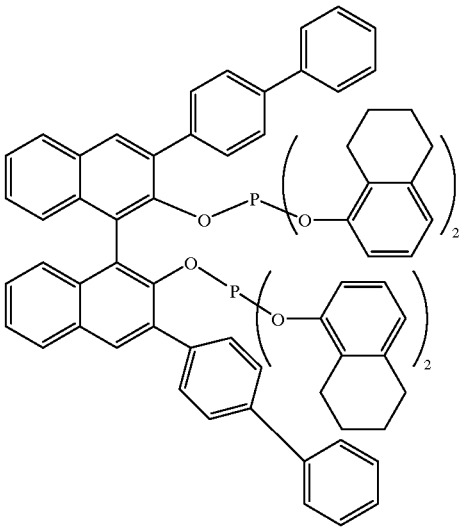

Under an atmosphere of nitrogen, a cold (−35° C.) anhydrous diethyl ether solution (5 mL) of 2,2'-dihydroxy-1,1'-binaphthalene-3,3'-bis(diphenyl) (0.050 g, 0.08 mmol) was added to the phosphochlorodite of 5,6,7,8-tetrahydro-1-naphthol (0.076 g, 0.21 mmol) dissolved in diethyl ether (5 mL). While maintaining this temperature, triethylamine (0.03 mL, 0.21 mmol) was added dropwise to the above mixture resulting in the formation of a white precipitate. After stirring at room temperature for three hours, the reaction mixture was filtered through a pad of basic alumina and Celite®. The filtrate was evaporated to yield the desired diphosphite as a white powder (0.043 g, 58%). $^{31}$P {$^1$H} NMR (202.4 MHz, C$_6$D$_6$): 127.83, 132.14, 132.60 (major), 133.66, 141.51, 143.99 ppm.

Hydrocyanation Results for the
Ligand of Example 2

Preparation of catalyst: A catalyst solution was prepared by adding 0.0039 g of Ni(COD)$_2$ (0.014 mmol) in 0.320 ml toluene to 0.062 g of the ligand of Example 2 (0.049 mmol) in 0.200 mL toluene Hydrocyanation of 3,4 Pentenenitrile (3,4 PN): 116 μl of the above catalyst solution (0.0031 mmol Ni), and 13 μl of a solution of ZnCl₂ in 3PN (0.0067 mmol ZnCl₂) were added to a vial fitted with a septum cap. The vial was cooled to −20° C. and 125 μl of a solution of HCN, t-3PN, and 2-ethoxyethyl ether (0.396 mmol HCN, 0.99 mmol t-3PN) was added. The vial was sealed and set aside for 24 hours at room temperature. The reaction mixture was diluted with ethyl ether and the product distribution analyzed by GC using 2-ethoxyethyl ether as an internal standard. Analysis showed that 22.7% of the starting pentenenitriles had been converted to dinitrile product (62.8% yield based on HCN.) The selectivity to the linear ADN isomer was 97.4%.

Hydrocyanation Results for the
Ligand of Example 3

Preparation of catalyst: A catalyst solution was prepared by adding 0.0039 g of Ni(COD)₂ (0.014 mmol) in 0.320 ml toluene to 0.025 g of the ligand of Example 3 (0.020 mmol) in 0.200 mL toluene Hydrocyanation of 3,4 Pentenenitrile (3,4 PN): 116 μl of the above catalyst solution (0.0031 mmol Ni), and 13 μl of a solution of ZnCl₂ in 3PN (0.0067 mmol ZnCl₂) were added to a vial fitted with a septum cap. The vial was cooled to −20° C. and 125 μl of a solution of HCN, t-3PN, and 2-ethoxyethyl ether (0.396 mmol HCN, 0.99 mmol t-3PN) was added. The vial was sealed and set aside for 24 hours at room temperature. The reaction mixture was diluted with ethyl ether and the product distribution analyzed by GC using 2-ethoxyethyl ether as an internal standard. Analysis showed that 9.2% of the starting pentenenitriles had been converted to dinitrile product (25.4% yield based on HCN.) The selectivity to the linear ADN isomer was 97.5%.

| Example # | Step 2 conv | Step 2 dist |
|---|---|---|
| 1 | 10.4 | 94.6 |
| 2 | 22.7 | 97.4 |
| 3 | 9.2 | 97.5 |

What is claimed is:

1. A hydrocyanation process comprising; reacting an acyclic, aliphatic, monoethylenically unsaturated compound in which the ethylenic double bond is not conjugated to any other olefinic group in the molecule with a source of HCN in the presence of a catalyst composition comprising a Lewis acid, a zero-valent nickel and at least one multidentate phosphite ligand selected from the group represented by the following formulae I II or III:

Formula I
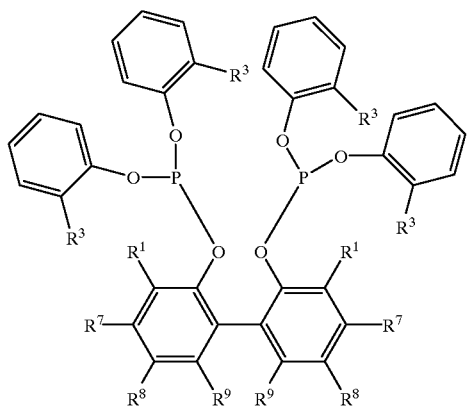

Formula II
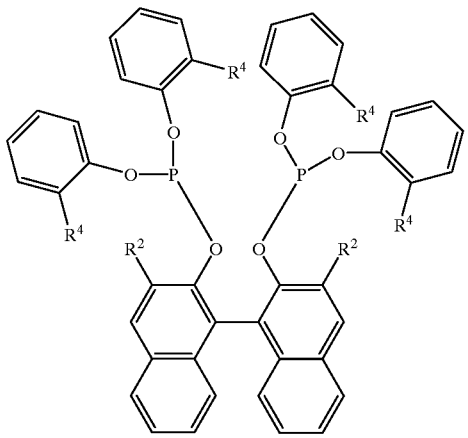

Formula III
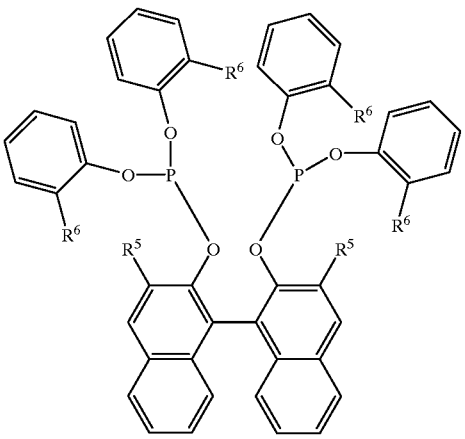

wherein
$R^1$ is independently $C_1$ to $C_{18}$ primary or secondary alkyl;
$R^2$ is independently aryl or substituted aryl;
$R^3$ is independently aryl or substituted aryl;
$R^4$ is independently $C_1$ to $C_{18}$ primary alkyl;
$R^5$ is hydrogen;
$R^6$ is independently aryl or substituted aryl;
$R^7$ is independently $C_1$ to $C_{18}$ primary or secondary alkyl;
$R^8$ is independently $C_1$ to $C_{18}$ primary or secondary alkyl;
$R^9$ is independently $C_1$ to $C_{18}$ primary or secondary alkyl; and
wherein other positions on the aromatic rings may also be substituted with alkyl, ether or ester groups, or combinations of two or more thereof.

2. The process of claim 1 wherein the starting ethylenically unsaturated compound is selected from the group consisting of 3-pentenenitrile, 4-pentenenitrile; alkyl 2-, 3-, and 4-pentenoates, and $C_zF_{2z+1}CH=CH_2$, wherein z is an integer of 1 to 12.

3. The process of claim 2 wherein the starting ethylenically unsaturated compound is 3-pentenenitrile or 4-pentenenitrile.

4. The process of claim 1 which is carried out at a temperature of −25° C. to 200° C. and at a pressure of 50.6 to 1013 kPa.

5. The process of claim 4 which is carried out at atmospheric pressure and at a temperature of 0° C. to 150° C.

6. The process of claim 1 wherein the Lewis acid is selected from the group consisting of inorganic or organometallic compounds in which the cation is selected from scandium, titanium, vanadium, chromium, manganese, iron, cobalt, copper, zinc, boron, aluminum, yttrium, zirconium, niobium, molybdenum, cadmium, rhenium and tin.

7. The process of claim 6 wherein the Lewis acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(tetrahydrofuran)_2$, $TiCl_4(tetrahydrofuran)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$ $(phenyl)_2AlCl$, $phenylAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $CdCl_2$, $B(C_6H_5)_3$, and $(C_6H_5)_3SnX$, wherein $X=CF_3SO_3$, $CH_3C_6H_5SO_3$, or $(C_6H_5)_3BCN$.

8. The process of claim 1 wherein the ligand has the structure of formula II, $R^2$ is substituted aryl and $R^4$ is cycloalkyl.

9. The process of claim 1 wherein the ligand has the structure of formula I and $R^3$ is unsubstituted phenyl.

10. The process of claim 9 wherein $R^1$, $R^7$ and $R^9$ are methyl.

11. The process of claim 9 wherein $R^1$, $R^8$ and $R^9$ are methyl.

12. The process of claim 1 having a product distribution of at least about 97%.

13. A multidentate phosphite ligand of the formulae I II or III:

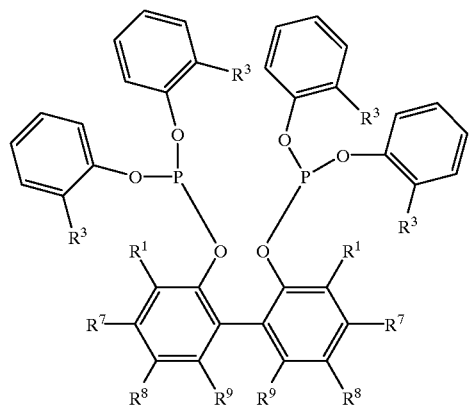

Formula I

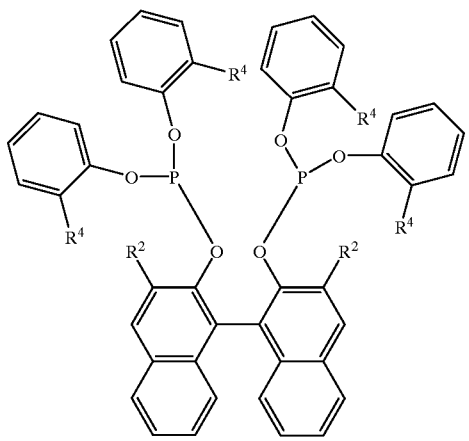

Formula II

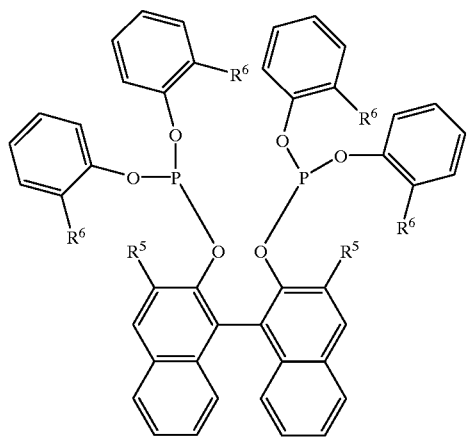

Formula III wherein $R^1$ is independently $C_1$ to $C_{18}$ primary or secondary alkyl;

$R^2$ is independently aryl or substituted aryl;

$R^3$ is independently aryl or substituted aryl;

$R^4$ is independently $C_1$ to $C_{18}$ primary alkyl;

$R^5$ is hydrogen;

$R^6$ is independently aryl or substituted aryl;

$R^7$ is independently $C_1$ to $C_{18}$ primary or secondary alkyl;

$R^8$ is independently $C_1$ to $C_{18}$ primary or secondary alkyl;

$R^9$ is independently $C_1$ to $C_{18}$ primary or secondary alkyl; and wherein other positions on the aromatic rings may also be substituted with alkyl, ether or ester groups, or combinations of two or more thereof.

14. The ligand of claim 13 wherein the ligand has the structure of formula II and $R^2$ is substituted aryl.

15. The ligand of claim 14 wherein $R^4$ is cycloalkyl.

16. The ligand of claim 13 having the structure of formula I wherein $R^3$ is unsubstituted phenyl.

17. The ligand of claim 16 wherein $R^1$, $R^7$ and $R^9$ are methyl.

18. The ligand of claim 16 wherein $R^1$, $R^8$ and $R^9$ are methyl.

* * * * *